United States Patent [19]

Lavielle et al.

[11] Patent Number: 5,723,484
[45] Date of Patent: Mar. 3, 1998

[54] BENZOPYRAN COMPOUNDS AS 5-HT$_{2C}$ RECEPTOR ANTAGONISTS

[75] Inventors: Gilbert Lavielle, La Celle Saint Cloud; Thierry Dubuffet, L'Hay les Roses; Mark Millan, Paris; Adrian Newman-Tancredi, Le Pecq, all of France

[73] Assignee: Adir et Compagnie, Courbevoie, France

[21] Appl. No.: 786,504

[22] Filed: Jan. 21, 1997

Related U.S. Application Data

[62] Division of Ser. No. 498,217, Jul. 5, 1995, Pat. No. 5,663,191.

[30] Foreign Application Priority Data

Jul. 6, 1994 [FR] France ................... 94.08328

[51] Int. Cl.$^6$ .................. A61K 31/40; C07D 491/52
[52] U.S. Cl. .................. 514/410; 514/338; 546/276.7; 548/421
[58] Field of Search ................. 548/421; 514/410, 514/338; 546/276.7

[56] References Cited

U.S. PATENT DOCUMENTS 3,518,272  6/1970  Strandtmann .................. 260/286

*Primary Examiner*—C. Warren Ivy
*Assistant Examiner*—Evelyn Huang
*Attorney, Agent, or Firm*—The Firm of Gordon W. Hueschen

[57] ABSTRACT

Compounds of formula (I):

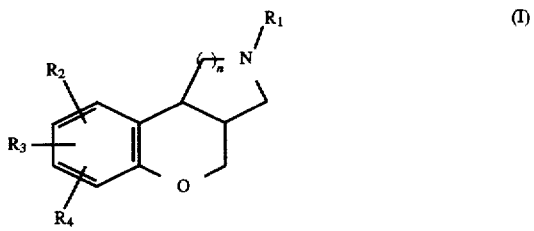

in which:

n represents 1 or 2.

$R_1$ represents hydrogen or alkyl, benzyl, acetyl, benzoyl, allyl, pyridinecarbonyl, pyridinemethyl, acylaminoalkyl (optionally substituted), pyridineaminocarbonyl, phthalimidoalkyl, thiochromanyloxyalkyl or (benzodioxanyloxy)alkyl.

$R_2$, $R_3$ or $R_4$, which may be identical or different, represent hydrogen or halogen or alkyl, alkoxy, hydroxyl, acetyl, aminocarbonyl, aminomethyl, cyano, nitro, amino, phenyl (which may or may not be substituted), furyl, pyridinyl, thienyl or pyridyl, or alternatively, when they are located on adjacent carbons, $R_2$ and $R_3$ form, with the carbon atoms which bear them, a furan or phenyl ring.

the isomers thereof and the addition salts thereof with a pharmaceutically acceptable acid, and medicinal products containing the same are useful for the treatment of diseases requiring a ligand to the 5-HT$_{2C}$ receptors.

7 Claims, No Drawings

BENZOPYRAN COMPOUNDS AS 5-HT$_{2C}$ RECEPTOR ANTAGONISTS

The present application is a division of our prior-filed application Ser. No. 08/498,217, filed Jul. 5, 1995, now U.S. Pat. No. 5,663,191 issued Sep. 2, 1997.

BACKGROUND OF THE INVENTION—PRIOR ART

Besides the fact that they are novel, the compounds of the present invention have particularly advantageous properties by selectively binding to the 5-HT$_{2C}$ serotoninergic receptors with respect to the 5-HT$_{2A}$ receptors. This novel property has never been demonstrated for the most closely related compounds of the prior art such as, for example, those described in patents WO 9006927, EP410,535, EP539, 209 or EP95666.

FIELD OF THE INVENTION

It is well established that the ascending serotoninergic, dopaminergic and adrenergic pathways projecting towards the limbic system and the cortex play a deciding role in controlling mood and in the etiology and treatment of psychiatric diseases such as schizophrenia, depression and anxiety, as well as aggression and other impulse disorders (M. J. Millan et al., Drug News & Perspectives, 5, 397–406, 1992; A. Y. Deutch et al., Schizophrenia, 4, 121–156, 1991; H. Y. Meltzer and J. F. Nash, Pharmacol. Rev., 43, 587–604, 1991). These pathways express their actions by a multitude of different receptors, and increasingly greater efforts are being made in order to identify the types of receptors involved in these diseases. It is thus hoped that by modifying their activity with agonists or antagonists, correction of disorders reflecting dysfunction of the monoaminergic systems may be achieved.

As regards serotonin (5-HT), at least 7 different types of receptors have been cloned, although present understanding at the functional level is fairly limited for several of them. Nevertheless, for the two subtypes of 5-HT$_2$ receptors which are present in the brain, 5-HT$_{2A}$ and 5-HT$_{2C}$, good indications exist that they are more particularly involved in controlling mood (J. F. W. Deakin, Pharmacol. Biochem. Behav., 29, 819–820, 1988) as well as in the modulation of several physiological functions such as the appetite (G. A. Kennett et al., Eur. J. Pharmacol., 164, 445–454, 1989), sleep (C. Dugovic et al., Psychopharmacology, 97, 436–442, 1989), sexual behavior (H. H. G. Berendsen et al., Psychopharmacology, 101, 57–61, 1990), motor activity (G. A. Kennett and G. Curzon, Psychopharmacology, 96, 93–100, 1988) and cardiovascular functioning (I. K. Anderson et al., Br. J. Pharmacol., 107, 1020–1028, 1992). Consequently, in animals, activation of the 5-HT$_{2C}$ receptors appears to bring about, for example, a decrease in the motor activity (I. Lucki et al., J. Pharmacol. Exp. Ther., 249, 155–164, 1989) and a reduction in food intake (S. J. Kitchener and C. T. Dourish, Psychopharmacology, 113, 369–377, 1994), whereas in animals or in man, antagonism of the 5-HT$_{2A/2C}$ receptors is associated with anxiolytic effects (G. A. Kennet et al., Eur. J. Pharmacol., 164, 445–454, 1989, D. L. S. Ceuleumans et al., Pharmacopsychiatry, 18, 303–305, 1985), antidepressant effects (F. Jenck et al., Eur. J. Pharmacol., 321,223–229, 1993) and anti-schizophrenic effects (D. L. S. Ceuleumans et al., J. Pharmacol. Exp. Ther., 85, 329–332, 1985). Moreover, blocking of the 5-HT$_{2A/2C}$ receptors appears to be involved in the atypical profile of the antipsychotic agent clozapine (A. Y. Deutch et al., Schizophrenia, 4, 121–156, 1991).

In view of their very great similarity, it has been extremely difficult to differentiate between the actions induced by the 5-HT$_{2A}$ receptors and those of the 5-HT$_{2C}$ receptors. Furthermore, for a long time, no antagonist existed which was selectively interactive with 5-HT$_{2A}$ receptors or with the 5-HT$_{2C}$ receptors. Thus, the recent discovery of a selective 5-HT$_{2A}$ antagonist, MDL 100,907, and of a selective 5-HT$_{2C}$ antagonist, SB 200,646, has aroused much interest (Sorensen et al., J. Pharmacol. Exp. Ther., 1993). The first results obtained with the compound SB 200,646 showing its anxiolytic properties allow a particularly important role of the 5-HT$_{2C}$ receptors to be envisaged in controlling mood (G. A. Kennett et al., Br. J. Pharmacol., 111, 797–802, 1994; G. A. Kennett et al., Eur. J. Pharmacol., 164, 445–454, 1989). This conviction is strongly reinforced by the clinical results obtained with mCPP, which behaves as a 5-HT$_{2C}$ agonist and a 5-HT$_{2A}$ antagonist (G. A. Kennett and G. Curzon, Br. J. Pharmacol., 94, 137–147, 1988; I. Lucki et al., J. Pharmacol. Exp. Ther., 249, 155–164, 1989; P. J. Conn and E. Sanders-Bush, J. Pharmacol. Exp. Ther., 242, 552–557, 1987), which possesses pronounced anxiogenic properties and which exacerbates depressive, aggressive and psychotic states in patients (D. L. Murphy et al., Psychopharmacology, 98, 275–282, 1989; J. H. Krystal et al., Soc. Neurosci. Abst., 17, 354, 1991; J. P. Seibyl, Soc. Neurosci. Abst., 15, 1236, 1989).

The compounds described in the present invention bind selectively to the 5-HT$_{2C}$ receptors with respect to the 5-HT$_{2A}$ receptors and are antagonists may thus be used in the treatment of diseases such as anxiety, depression, impulse disorders (such as aggression, B. A. McMillen, Drug. Develop. Persp., 12, 53–62, 1988), schizophrenia, appetite disorders (such as anorexia), cardiovascular diseases, sexual dysfunction (H. H. G. Berendsen et al., Psychopharmacology, 101, 57–61, 1990), cerebral ischemic attacks (F. Granier et al., Acta Psychiatr. Scand., 72, 67–74, 1985; W. D. Dietrich et al., J. Cereb. Blood Flow Metabol., 9, 812–820, 1989; J. A. Zivin, Neurology, 34, 469–474, 1984; J. A. Zivin, Neurology, 35, 584–587, 1985; K. M. Bode-Greuel et al., Stroke, 21, 164–166, 1990), drug abuse (T. F. Meert and P. A. J. Janssen, Drug. Develop. Res., 25, 39–53, 1992; T. F. Meert and P. A. J. Janssen, Drug. Develop. Res., 25, 55–66, 1992; E. M. Sellers et al., Trends Pharmacol. Sci., 13, 69–75, 1992), sleeping disorders (C. Dugovic et al., Psychopharmacology, 97, 436–442, 1989) and migraine (D. L. Murphy et al., Psychopharmacology, 98, 275–282, 1989).

DETAILED DESCRIPTION OF THE INVENTION

More specifically, the present invention relates to the compounds of formula (I):

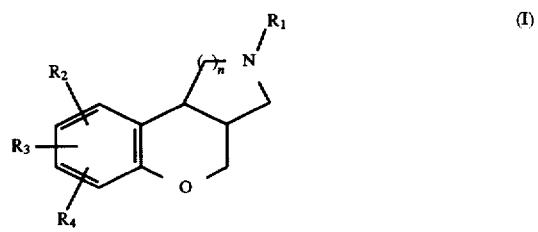

in which:

n represents 1 or 2,

R$_1$ represents a hydrogen atom or a linear or branched (C$_1$–C$_6$) alkyl group, a benzyl, acetyl, benzoyl, allyl, pyridinecarbonyl or pyridinemethyl group, a pyridineaminocarbonyl group, a linear or branched $(C_1-C_6)$ phthalimidoalkyl group, a linear or branched $(C_1-C_4)$ (thiochroman-8-yloxy)alkyl group, a linear or branched $(C_1-C_4)$ (benzodioxanyloxy)alkyl group or a linear or branched $(C_1-C_6)$ acylaminoalkyl group, (wherein acyl is a benzoyl group, a naphtylcarbonyl group, a thienylcarbonyl group, a linear or branched $(C_1-C_6)$ alkylcarbonyl group, a furylcarbonyl group, a pyrrolylcarbonyl group, a pyridinylcarbonyl group, or a $(C_3-C_7)$ cycloalkylcarbonyl group, each of these groups being optionally substituted with one or more halogen atoms, trihalomethyl group, alkoxy group or hydroxy group), $R_2$, $R_3$ or $R_4$, which may be identical or different, represent a hydrogen or halogen atom or a linear or branched $(C_1-C_6)$ alkyl group, a linear or branched $(C_1-C_6)$ alkoxy group, a hydroxyl, acetyl, aminocarbonyl, aminomethyl, cyano, nitro or amino group, a phenyl group (which may or may not be substituted with one or more halogen atoms or hydroxyl groups, linear or branched $(C_1-C_6)$ alkoxy groups, linear or branched $(C_1-C_6)$ alkyl groups or trihalomethyl groups), a furyl group, a pyridinyl group, a thienyl group or a pyrrolyl group, or alternatively, when they are located on adjacent carbons, $R_2$ and $R_3$ form, with the carbon atoms which bear them, a furan or phenyl ring, the isomers thereof and the addition salts thereof with a pharmaceutically acceptable acid.

Among the pharmaceutically acceptable acids which may be mentioned, without any limitation, are hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, camphoric acid, etc.

The invention also relates to the process for the preparation of the compounds of formula (I). In this process, when the compounds of formula (I) which it is desired to obtain are such that n=1, a pyrrolidine of formula (II) is used as starting material, in the form of a pair of enantiomers or a pure enantiomer:

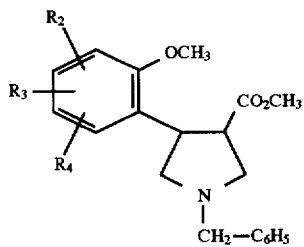
(II)

in which $R_2$, $R_3$ and $R_4$ are as defined in formula (I), which compound of formula (II), when it is in the form of a pair of enantiomers, is reacted with lithium aluminum hydride in an inert solvent to give the pyrrolidine of formula (III):

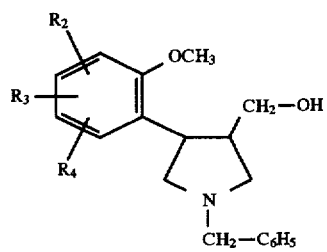
(III)

in which $R_2$, $R_3$ and $R_4$ have the same meaning as in formula (I), the methoxy function of which is converted into a hydroxyl function by reaction in the presence of sodium thioethoxide or boron tribromide, and which is then reacted with gaseous hydrogen chloride in the presence of thionyl chloride, in chloroform medium, to give the compound of formula (IV):

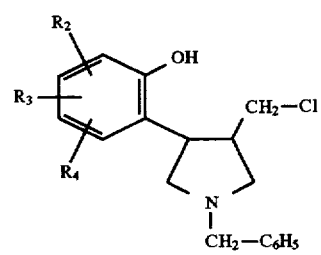
(IV)

in which $R_2$, $R_3$ and $R_4$ have the same meaning as in formula (I), which compound is then cyclized in basic medium, to give the compound of formula (I/a), a particular case of the compounds of formula (I):

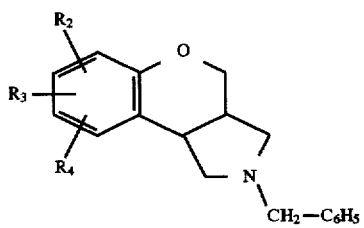
(I/a)

in which $R_2$, $R_3$ or $R_4$ have the same meaning as in formula (I), compound of formula (I/a), the amine function of which may be deprotected, if so desired, by catalytic hydrogenation, to give the compound of formula (I/b), a particular case of the compounds of formula (I):

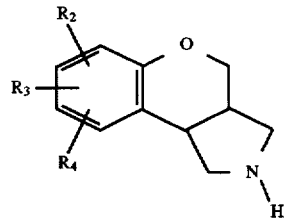
(I/b)

in which $R_2$, $R_3$ and $R_4$ have the same meaning as in formula (I), which compound of formula (I/b) may be reacted, if so desired, with a halo derivative:

R'$_1$X in which:

X represents a halogen atom and

R'$_1$ represents a linear or branched (C$_1$–C$_6$) alkyl group, an acetyl, benzoyl, pyridinecarbonyl, pyridinemethyl or 3-pyridineaminocarbonyl group or a linear or branched (C$_1$–C$_6$) phthalimidoalkyl group, to give either the compound of formula (I/c), a particular case of the compounds of formula (I):

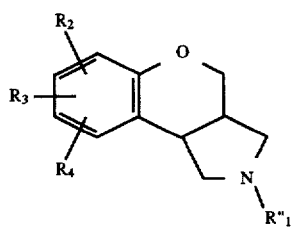

(I/c)

in which

R$_2$, R$_3$ and R$_4$ have the same meaning as in formula (I) and R"$_1$ represents a linear or branched (C$_1$–C$_6$) alkyl group, an acetyl, benzoyl, pyridinecarbonyl, pyridinemethyl or 3-pyridineaminocarbonyl group or a linear or branched (C$_1$–C$_6$) phthalimidoalkyl group, or the compound of formula (V):

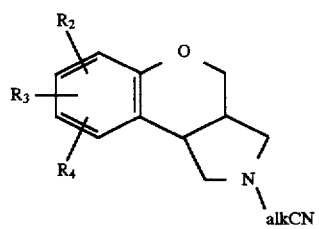

(V)

in which

R$_2$, R$_3$ and R$_4$ have the same meaning as in formula (I) and alkCN represents a linear or branched (C$_1$–C$_6$) cyanoalkyl group, compound of formula (V), the cyano group of which is reduced to an amino group and which is reacted with a benzoyl halide (optionally substituted with a halogen atom), to give the compound of formula (I/d), a particular case of the compounds of formula (I):

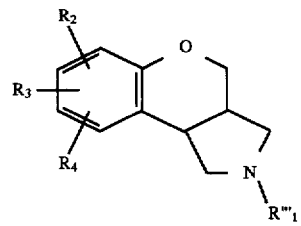

(I/d)

in which

R$_2$, R$_3$ and R$_4$ have the same meaning as in formula (I) and R'''$_1$ represents a linear or branched (C$_1$–C$_6$) benzoylaminoalkyl group (optionally substituted on the phenyl ring with a halogen atom), which compound of formula (I/a), (I/b), (I/c) or (I/d):

is optionally purified according to a standard purification technique, whose enantiomers are separated, if so desired, according to a standard separation technique, and which is converted, where appropriate, into the addition salts thereof with a pharmaceutically acceptable acid.

it being understood that the substituents R$_2$, R$_3$ and R$_4$ may be introduced or modified throughout the synthesis of the compounds of formula (I), according to standard techniques in organic chemistry.

The compounds of formula (II) used as starting materials are prepared according to the process described by K. Achiwa et al. (Chem. Pharm. Bull., 33(7), 2762–2766, 1985) by performing a cycloaddition of an ethylene of formula (IIa):

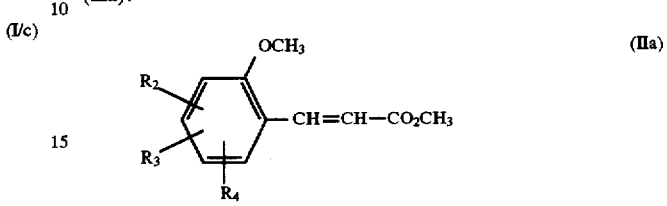

(IIa)

in which

R$_2$, R$_3$ and R$_4$ have the same meaning as in formula (I), with N-benzyl-N-(methoxymethyl) trimethylsilylmethylamine in the presence of a catalyst such as trifluoroacetic acid. Depending on the configuration of the ethylene of formula (IIa) used, this cycloaddition gives a pyrrolidine of formula (II) in which the hydrogen atoms located in positions 3 and 4 are cis or trans relative to each other.

The compounds of formula (IV) may also be obtained, when the pyrrolidine possesses hydrogen atoms in a cis position relative to each other, by performing a cycloaddition according to the process described by K. Achiwa et al. (cited above) of a coumarin of formula (VI):

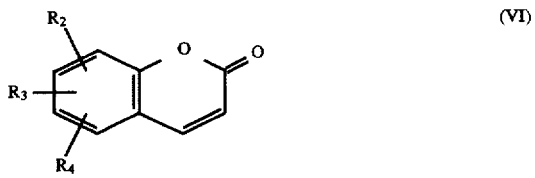

(VI)

in which

R$_2$, R$_3$ and R$_4$ have the same meaning as in formula (I), with N-benzyl-N-(methoxymethyl) trimethylsilylmethylamine, using trifluoroacetic acid as catalyst, to give the compound of formula (VII):

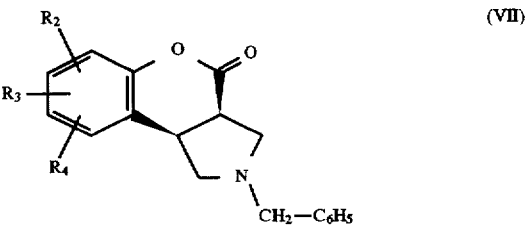

(VII)

in which

R$_2$, R$_3$ and R$_4$ have the same meaning as in formula (I), which compound then undergoes a reduction in the presence of lithium aluminum hydride, to give the compound of formula (VIII):

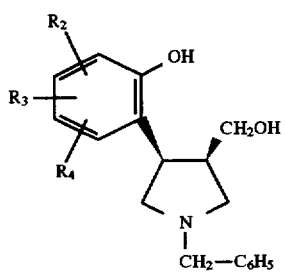

(VIII)

which is reacted with gaseous hydrogen chloride in the presence of thionyl chloride, to give the compound of formula (IV).

In the process for the preparation of the compounds of formula (I), for which n=2, the starting material used is the compound of formula (IX):

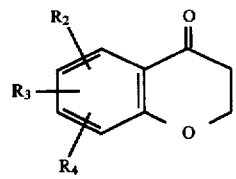

(IX)

in which $R_2$, $R_3$ and $R_4$ are as defined in formula (I), which compound is reacted, according to the method described in Can. J. Chem., 52, 2316, 1974, with methylmagnesium bromide and then with p-toluenesulfonic acid, to give the compound of formula (X):

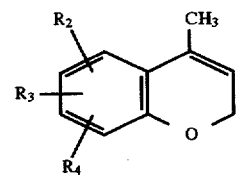

(X)

in which $R_2$, $R_3$ and $R_4$ have the same meaning as in formula (I), which compound is reacted with benzylamine in the presence of formaldehyde, to give the compound of formula (XI):

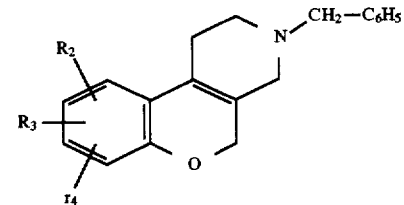

(XI)

in which $R_2$, $R_3$ and $R_4$ have the same meaning as in formula (I), which compound then undergoes a catalytic hydrogenation to give the compound of formula (I/e), a particular case of the compounds of formula (I):

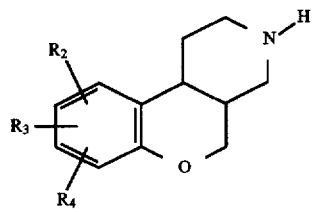

(I/e)

in which $R_2$, $R_3$ and $R_4$ have the same meaning as in formula (I), which compound of formula (I/e) may be reacted, if so desired, with a halo derivative of formula (XII):

$R'_{1A}—X$ (XII)

in which:

X represents a halogen atom and $R'_{1A}$ represents a linear or branched ($C_1$–$C_6$) alkyl group, an acetyl, benzoyl, benzyl, pyridinecarbonyl, pyridinemethyl or 3-pyridineaminocarbonyl group or a linear or branched ($C_1$–$C_6$) phthalimidoalkyl group, to give either the compound of formula (I/f), a particular case of the compounds of formula (I):

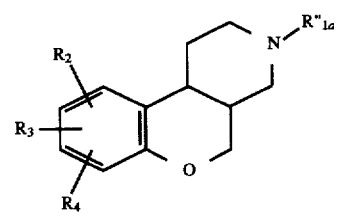

(I/f)

in which $R_2$, $R_3$ and $R_4$ have the same meaning as in formula (I) and $R''_{1A}$ represents a linear or branched ($C_1$–$C_6$) alkyl group, an acetyl, benzoyl, benzyl, pyridinecarbonyl, pyridinemethyl or 3-pyridineaminocarbonyl group or a linear or branched ($C_1$–$C_6$) phthalimidoalkyl group, or the compound of formula (XIII):

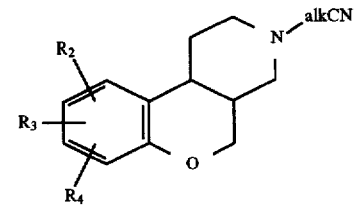

(XIII)

in which $R_2$, $R_3$ and $R_4$ have the same meaning as in formula (I) and alkCN represents a linear or branched ($C_1$–$C_6$) cyanoalkyl group compound of formula (XIII), the cyano group of which is reduced to an amino group and which is reacted with a benzoyl halide (optionally substituted with a halogen atom), to give the compound of formula (I/g), a particular case of the compounds of formula (I):

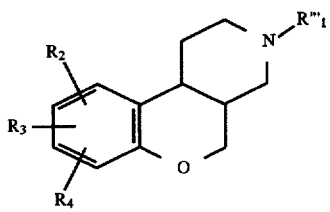

in which

R$_2$, R$_3$ and R$_4$ have the same meaning as in formula (I) and R'''$_1$ represents a linear or branched (C$_1$–C$_6$) benzoylaminoalkyl group (optionally substituted on the phenyl ring with a halogen atom), which compound of formula (I/e), (I/f) or (I/g):

- is optionally purified according to a standard purification technique,
- whose enantiomers are separated, if so desired, according to a standard separation technique,
- and which is converted, where appropriate, into the addition salts thereof with a pharmaceutically acceptable acid,
- it being understood that the substituents R$_2$, R$_3$ and R4 may be introduced or modified throughout the synthesis of the compounds of formula (I), according to standard techniques in organic chemistry.

Another subject of the present invention is the pharmaceutical compositions containing, as active principle, at least one compound of formula (I) alone or in combination with one or more inert, non-toxic excipients or vehicles.

Among the pharmaceutical compositions according to the invention, there may more particularly be mentioned those which are suitable for oral, parenteral and nasal administration, simple or coated tablets, sublingual tablets, gelatin capsules, lozenges, suppositories, creams, ointments, dermal gels, etc.

The appropriate dosage varies depending on the age and weight of the patient, the nature and severity of the complaint and the route of administration. The latter may be an oral, nasal, rectal or parenteral route. In general, the unit dosage ranges between 1 and 500 mg for a treatment of 1 to 3 doses taken per 24 hours.

The examples which follow illustrate the invention and do not limit it in any way.

The structures of the compounds described in the examples were confirmed by the usual spectroscopic techniques.

The position of the hydrogen atoms located between the two heterocycles is indicated in the following way:

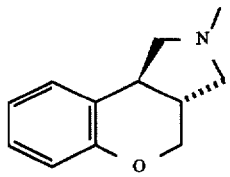

trans-1,3,3a,4,9b-Pentahydrobenzopyrano[3,4-c]pyrrole

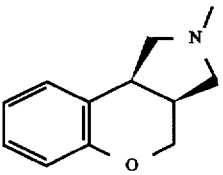

cis-1,3,3a,4,9b-Pentahydrobenzopyrano[3,4-c]pyrrole

The preparations described below lead to starting materials used during the synthesis of the compounds of the invention.

Preparation A:

Methyl[trans-1-benzyl-4-(2-methoxyphenyl) pyrrolidin-3-yl]carboxylate

The expected product is obtained according to the process described by K. Achiwa et al. (Chem. Pharm. Bull., 33(7), 2762–2766, 1985). To a solution containing 120 mmol of methyl trans-(2-methoxy)cinnamate and 0.1 ml of trifluoroacetic acid in 150 ml of ethyl acetate cooled to 5° C., are slowly added 100 mmol of N-benzyl-N-(methoxy-methyl) trimethylsilylmethylamine. The reaction medium is brought from 30° C. to 55° C. the over 75 minutes. 0.75 g of potassium carbonate is then added and the mixture is kept stirring for 15 minutes. After filtration and evaporation of the solvents, the residue is taken up in 100 ml of ethyl acetate and the solution is brought to 50° C. 110 mmol of oxalic acid dissolved in 100 ml of acetone are then added with vigorous stirring. The stirring is continued for 15 hours. The expected product in the form of the oxalate is then obtained after filtration, and is rinsed with ether. The base is obtained after treatment of the oxalate with two equivalents of 1N potassium hydroxide.

Infrared: $v_{CO}$ (nujol)=1736 cm$^{-1}$

Preparation B:

Methyl[trans-1-benzyl-4-(2,6-dimethoxyphenyl) pyrrolidin-3-yl]carboxylate

The expected product is obtained according to the process described in Preparation A, using methyl trans-(2,6-dimethoxy)cinnamate as starting material.

Infrared: $v_{CO}$ (nujol)=1736 cm$^{-1}$

Preparation C:

Methyl[trans-1-benzyl-4-(2,5-dimethoxyphenyl) pyrrolidin-3-yl]carboxylate

The expected product is obtained according to the process described in Preparation A, using methyl trans-(2,5-dimethoxy)cinnamate as starting material.

Infrared: $v_{CO}$ (nujol)=1736 cm$^{-1}$

Preparation D:

cis-2-Benzyl-1,3,3a,9b-tetrahydrobenzopyrano[3,4-c]pyrrol-4-one

The expected product is obtained according to the process described in Preparation A, using coumarin as starting material.

Melting point (oxalate): 170°–175° C.

Preparation E:

Methyl[cis-1-benzyl-4-(2,6-dimethoxyphenyl) pyrrolidin-3-yl]carboxylate

The expected product is obtained according to the process described in Preparation A, using methyl cis-(2,6-dimethoxy)cinnamate as starting material.

11

Infrared: $\nu_{CO}$ (nujol)=1757 cm$^{-1}$

Preparation F:

Methyl[trans-1-benzyl-4-(2-methoxy-4-chlorophenyl)pyrrolidin-3-yl]carboxylate

The expected product is obtained according to the process described in Preparation A, using methyl trans-(2-methoxy-4-chloro)cinnamate as starting material.

Infrared: $\nu CO$(nujol)=1755 cm$^{-1}$

Preparation G:

cis-2-Benzyl-7-methoxy-1,3,3a,9b-tetrahydrobenzopyrano[3,4-c]pyrrol-4-one

The expected product is obtained according to the process described in Preparation A, using 7-methoxycoumarin as starting material.

Melting point (oxalate): 182°–186° C.

Preparation H:

Methyl[trans-1-benzyl-4-(2,4-dimethoxyphenyl)pyrrolidin-3-yl]carboxylate

The expected product is obtained according to the process described in Preparation A, using methyl trans-(2,4-dimethoxy)cinnamate as starting material.

Preparation I:

Methyl[trans-1-benzyl-4-(2,3-dimethoxyphenyl)pyrrolidin-3-yl]carboxylate

The expected product is obtained according to the process described in Preparation A, using methyl trans-(2,3-dimethoxy)cinnamate as starting material.

Preparation J:

cis-2-Benzyl-8-chloro-1,3,3a,9b-tetrahydrobenzopyrano[3,4-c]pyrrol-4-one

The expected product is obtained according to the process described in Preparation A, using 6-chlorocoumarin as starting material.

Melting point (oxalate): 197° C.

Preparation K:

Methyl[trans-1-benzyl-4-(2-methoxy-5-chlorophenyl)pyrrolidin-3-yl]carboxylate

The expected product is obtained according to the process described in Preparation A, using methyl trans-(2-methoxy-5-chloro)cinnamate as starting material. Melting point (oxalate): 144° C.

Preparation L:

cis-2-Benzyl-6-chloro-1,3,3a,9b-tetrahydrobenzopyrano[3,4-c]pyrrol-4-one

The expected product is obtained according to the process described in Preparation A, using 8-chlorocoumarin as starting material.

Preparation M:

Methyl[trans-1-benzyl-4-(2-methoxy-3-chlorophenyl)pyrrolidin-3-yl]carboxylate

The expected product is obtained according to the process described in Preparation A, using methyl trans-(2-methoxy-3-chloro)cinnamate as starting material.

Preparation N:

Methyl[trans-1-benzyl-4-(2-methoxy-5-bromophenyl)pyrrolidin-3-yl]carboxylate

The expected product is obtained according to the process described in Preparation A, using methyl trans-(2-methoxy-5-bromo)cinnamate as starting material.

12

Preparation O:

Methyl[trans-1-benzyl-4-(2-methoxynaphth-1-yl)pyrrolidin-3-yl]carboxylate

The expected product is obtained according to the process described in Preparation A, using methyl trans-3-(2-methoxynaphth-1-yl)acrylate as starting material.

Preparation P:

Methyl[trans-1-benzyl-4-(1-methoxynaphth-2-yl)pyrrolidin-3-yl]carboxylate

The expected product is obtained according to the process described in Preparation A, using methyl trans-3-(1-methoxynaphth-1-yl)acrylate as starting material.

Preparation Q:

cis-16-Benzyl-13,14,15,17-tetrahydro-11-oxa-12-one-16-azacyclopenta[a]phenanthrene The expected product is obtained according to the process described in Preparation A, using benzo[h]chroman-2-one as starting material.

Preparation R:

cis-2-Benzyl-1,3,3a,11c-pentahydro-4-one-5-oxa-2-azacyclopenta[c]phenanthrene

The expected product is obtained according to the process described in Preparation A, using benzo[f]chromen-3-one as starting material.

EXAMPLE 1 trans-2-Benzyl-1,3,3a,4,9b-pentahydro-(1)-benzopyrano[3,4-c]pyrrole hydrochloride Stage A: trans-1-Benzyl-3-hydroxymethyl-4-(2-methoxyphenyl)pyrrolidine To 560 mmol of lithium aluminum hydride in 800 ml of tetrahydrofuran (THF), under a nitrogen atmosphere and at 5° C., are added 225 mmol of methyl [trans-1-benzyl-4-(2-methoxyphenyl)pyrrolidin-3-yl]carboxylate (described in Preparation A) dissolved in 500 ml of THF. After stirring for 1 hour at 5° C., 139 ml of isopropyl alcohol are added slowly to the above mixture, followed by 85.2 ml of saturated sodium chloride solution. The mixture is stirred slowly at room temperature. After filtration and evaporation of the solvents, the expected product is obtained.

Stage B: trans-1-Benzyl-3-hydroxymethyl-4-(2-hydroxyphenyl)pyrrolidine

To a previously prepared solution containing 96 mmol of sodium thioethoxide in 140 ml of dimethylformamide (DMF) are added slowly 24 mmol of the compound obtained in the above stage dissolved in 120 ml of DMF. The mixture is maintained at 120° C. for 4 hours. After cooling, dilution with water, extraction with ether, drying and evaporation, the expected product is obtained.

Stage C: trans-1-Benzyl-3-chloromethyl-4-(2-hydroxyphenyl)pyrrolidine hydrochloride 4.6 mmol of the compound obtained in the above stage are dissolved in 100 ml of chloroform. After sparging for 10 minutes with hydrogen chloride gas, the reaction medium is brought to reflux and 13.8 mmol of thionyl chloride are then added. The reflux is maintained until gaseous evolution has ceased. After evaporation of the solvent, the residue is taken up in ethanol and then evaporated. The expected product then precipitates in ether.

Stage D: trans-2-Benzyl-1,3,3a,4,9b-pentahydro-(1)-benzopyrano[3,4-c]pyrrole hydrochloride 2.95 mmol of the compound obtained in the above stage are dissolved in 100 ml of THF and 10 ml of hexamethylphosphorotriamide (HMPT). 4 ml of a 1.6M solution of butyllithium in hexane are then added to the above mixture. The mixture is kept stirring for 15 hours. After hydrolysis and evaporation of the solvents, the residue is taken up in water and extracted with ether. After drying and evaporation of the organic phases, the expected product is obtained by purification of the residue by column chromatography on silica, using a dichloromethane/methanol mixture (97/3) as eluent. The base is salified in hydrochloric ethanol.

Elemental microanalysis:

|  | C % | H % | N % | Cl % |
|---|---|---|---|---|
| calculated | 71.63 | 6.68 | 4.64 | 11.75 |
| found | 71.31 | 6.61 | 4.70 | 12.04 |

EXAMPLE 2 trans-2-Benzyl-9-hydroxy-1,3,3a,4,9b-pentahydro-(1)-benzopyrano[3,4-c]pyrrole hydrochloride Stage A: trans-1-Benzyl-3-hydroxymethyl-4-(2,6-dimethoxyphenyl)pyrrolidine The expected product is obtained according to the process described in Stage A of Example 1, using methyl[trans-1-benzyl-4-(2,6-dimethoxyphenyl)pyrrolidin-3-yl]carboxylate, described in Preparation B, as starting material.

Stage B: trans-1-Benzyl-3-chloromethyl-4-(2,6-dimethoxyphenyl)pyrrolidine

The expected product is obtained according to the process described in Stage C of Example 1.

Stage C: trans-1-Benzyl-3-chloromethyl-4-(2,6-dihydroxyphenyl)pyrrolidine

To 5.8 mmol of the compound obtained in the above stage, dissolved in 100ml of dichloromethane, are added 29 ml of a 1M solution of boron tribromide in dichloromethane. The mixture is maintained at reflux for 5 hours. After cooling, 77 ml of ethyl ether and then 200 ml of saturated sodium hydrogen carbonate solution are added. After extraction with ether, the organic phases are washed with saturated sodium hydrogen carbonate solution, dried and evaporated. The expected product is obtained after purification of the residue by column chromatography on silica, using a cyclohexane/ethyl acetate mixture (80/20) as eluent.

Stage D: trans-2-Benzyl-9-hydroxy-1,3,3a,4,9b-pentahydro-(1)-benzopyrano[3,4-c]pyrrole hydrochloride The expected product is obtained according to the process described in Stage D of Example 1.

Elemental microanalysis:

|  | C % | H % | N % | Cl % |
|---|---|---|---|---|
| calculated | 68.09 | 6.03 | 4.41 | 11.17 |
| found | 67.73 | 6.35 | 4.41 | 4.27 |

EXAMPLE 3 trans-2-Benzyl-9-methoxy-1,3,3a,4,9b-pentahydro-(1)-benzopyrano[3,4-c]pyrrole hydrochloride Stages A and B: These stages are identical to Stages A and B of Example 2.

Stage C: trans-1-Benzyl-3-chloromethyl-4-(2-hydroxy-6-methoxyphenyl)pyrrolidine

To 28.9 mmol of the compound obtained in the above stage, dissolved in 200 ml of dichloromethane, are added 57.8 ml of a 1M solution of boron tribromide in dichloromethane. The reaction medium is maintained at reflux for 45 minutes. After cooling and addition of 800 ml of water, the pH is brought to 10. After extraction with dichloromethane, drying and evaporation, the residue is purified by column chromatography on silica, using dichloromethane as eluent. The expected product is obtained after releasing with methanol and then with 1N sodium hydroxide.

Stage D: trans-2-Benzyl-9-methoxy-1,3,3a,4,9b-pentahydro-(1)-benzopyrano[3,4-c]pyrrole hydrochloride To 9.3 mmol of sodium hydride in 20 ml of THF is added a solution containing 7.8 mmol of the compound obtained in the above stage in 20 ml of THF. The reaction medium is maintained at reflux for 3 hours and then hydrolyzed. After extraction with ether, drying and evaporation, the expected product is obtained by purification of the residue by column chromatography on silica, using a dichloromethane/methanol mixture (95/5) as eluent.

Elemental microanalysis

|  | C % | H % | N % | Cl % |
|---|---|---|---|---|
| calculated | 68.77 | 6.68 | 4.22 | 10.68 |
| found | 68.34 | 6.47 | 4.51 | 11.21 |

EXAMPLE 4 trans-9-Methoxy-1,3,3a,4,9b-pentahydro-(1)-benzopyrano[3,4-c]pyrrole hydrochloride 2.2 mmol of the compound obtained in Example 3 in 100 ml of ethanol and 30 ml of water are hydrogenated for 1 hour at 45° C. in the presence of 70 mg of palladium-on-charcoal as catalyst. The expected product is obtained after evaporation of the solvents.

Elemental microanalysis

|  | C % | H % | N % | Cl % |
|---|---|---|---|---|
| calculated | 59.63 | 6.63 | 5.79 | 14.67 |
| found | 58.93 | 6.09 | 5.85 | 15.14 |

EXAMPLE 5 trans-2-Acetyl-9-methoxy-1,3,3a,4,9b-pentahydro-(1)-benzopyrano[3,4-c]pyrrole

To 0.8 mmol of the compound obtained in Example 4 in 30 ml of chloroform are successively added 1.66 mmol of triethylamine and then 0.8 mmol of acetyl chloride. After stirring for one hour at room temperature, the reaction medium is hydrolyzed. After extraction with chloroform, drying and evaporation, the expected product is obtained after crystallization of the residue from ethyl ether.

Elemental microanalysis:

|  | C % | H % |
|---|---|---|
| calculated | 68.00 | 6.93 |
| found | 67.21 | 6.57 |

EXAMPLE 6 trans-2-Propyl-9-methoxy-1,3,3a,4,9b-pentahydro-(1)-benzopyrano[3,4-c]pyrrole

To 3.3 mmol of the compound obtained in Example 4, dissolved in 20 ml of acetonitrile and 10 ml of acetone, are successively added 6.6 mmol of potassium carbonate and then 3.3 mmol of 1-bromopropane. The reaction medium is maintained at reflux for 15 hours. After cooling, filtration, hydrolysis and extraction with dichloromethane, the organic phases are dried and then evaporated. The expected product is obtained after purification of the residue by column chromatography on silica, using a dichloromethane/methanol/aqueous ammonia mixture (90/10/0.5) as eluent. The base thus obtained is salified in hydrochloric ethanol.

Melting point: 233° C.

Elemental microanalysis:

|  | C % | H % | N % | Cl % |
| --- | --- | --- | --- | --- |
| calculated | 63.48 | 7.81 | 4.94 | 12.45 |
| found | 63.53 | 7.86 | 4.84 | 12.74 |

EXAMPLE 7 trans-2-Allyl-9-methoxy-1,3,3a,4,9b-pentahydro-(1)-benzopyrano[3,4-c]pyrrole

To 3.3 mmol of the compound obtained in Example 4, dissolved in 30 ml of chloroform, are successively added 6.6 mmol of triethylamine and then 3.3 mmol of allyl bromide. The reaction medium is maintained at reflux for one hour and then hydrolyzed with 1N sodium hydroxide. After extraction with chloroform, the organic phases are combined, dried and evaporated. The expected product is obtained after purification of the residue by column chromatography on silica, using a dichloromethane/methanol/aqueous ammonia mixture (95/5/0.5) as eluent.

Elemental microanalysis:

|  | C % | H % | N % |
| --- | --- | --- | --- |
| calculated | 63.15 | 6.35 | 3.87 |
| found | 61.59 | 6.41 | 3.88 |

EXAMPLE 8 trans-2-[3-(4-Fluorobenzoylamino)ethyl]-9-methoxy-1,3,3a,4,9b-pentahydro-(1)-benzopyrano[3,4-c]pyrrole Stage A: trans-2-Cyanomethyl-9-methoxy-1,3,3a,4,9b-pentahydro-(1)-benzopyrano[3,4-c]pyrrole To 4.14 mmol of the compound obtained in Example 4, dissolved in 20 ml of acetonitrile, are successively added 8.28 mmol of potassium carbonate and then a solution containing 4.14 mmol of bromoacetonitrile in 20 ml of acetonitrile. The reaction medium is maintained at reflux for 15 hours. After cooling and filtration the filtrate is hydrolyzed and extracted with dichloromethane. The organic phases are dried and evaporated, and the expected product is obtained after purification of the residue by column chromatography on silica, using a dichloromethane/methanol mixture (98/2) as eluent.

Stage B: trans-2-(2-Aminoethyl)-9-methoxy-1,3,3a,4,9b-pentahydro-(1)-benzopyrano[3,4-c]pyrrole 1.5 mmol of the compound obtained in the above stage are added to a solution containing 3 mmol of lithium aluminum hydride in 15 ml of THF at 5° C. The reaction medium is stirred for 90 minutes at this temperature. After addition of 0.17 ml of water, 0.25 ml of 2N sodium hydroxide and then 0.46 ml of water, the medium is again stirred for 3 hours and then filtered. The solvents are evaporated off and the expected product is obtained after purification of the residue by column chromatography on silica, using a dichloromethane/methanol/aqueous ammonia mixture (80/20/2) as eluent.

Stage C: trans-2-[3-(4-Fluorobenzoylamino)ethyl]-9-methoxy-1,3,3a,4,9b-pentahydro-(1)-benzopyrano[3,4-c]pyrrole To 1 mmol of the compound obtained in the above stage, dissolved in 80 ml of chloroform at 5° C., are added 1 mmol of triethylamine and then, after stirring for 15 minutes, 1 mmol of para-chlorobenzoyl chloride. The reaction medium is maintained at 5° C. for 90 minutes and then hydrolyzed using 1N sodium hydroxide. After extraction with dichloromethane, the organic phases are dried and evaporated, and the expected product is obtained after purification of the residue by column chromatography on silica. The base is then salified in hydrochloric ethanol and the hydrochloride crystallizes from pentane.

Melting point: 202° C.

Elemental microanalysis:

|  | C % | H % | N % | Cl % |
| --- | --- | --- | --- | --- |
| calculated | 61.99 | 5.95 | 6.88 | 8.71 |
| found | 61.85 | 5.91 | 6.92 | 8.52 |

EXAMPLE 9 trans-2-Benzyl-8-methoxy-1,3,3a,4,9b-pentahydro-(1)-benzopyrano[3,4-c]pyrrole hydrochloride Stage A: trans-1-Benzyl-3-hydroxymethyl-4-(2,5-dimethoxyphenyl)pyrrolidine The expected product is obtained according to the process described in Stage A of Example 1, starting with methyl [trans-1-benzyl-4-(2,5-dimethoxyphenyl)pyrrolidin-3-yl] carboxylate described in Preparation C.

Stage B: trans-1-Benzyl-3-hydroxymethyl-4-(2-hydroxy-5-methoxyphenyl)pyrrolidine 97 mmol of ethanethiol are added to a solution containing 97 mmol of sodium hydride in 150 ml of DMF at 10° C. After stirring for 15 minutes at this temperature, 24 mmol of the compound obtained in Stage A are added and the reaction medium is maintained at 120° C. for 3 hours. After cooling, hydrolysis, extraction with ether and then with dichloromethane, the organic phases are combined, dried and evaporated. The expected product is obtained after purification by column chromatography on silica, using a dichloromethane/methanol mixture (95/5) as eluent.

Stage C: trans-1-Benzyl-3-chloromethyl-4-(2-hydroxy-5-methoxyphenyl)pyrrolidine

The expected product is obtained according to the process described in Stage C of Example 1, starting with the compound obtained in the above stage.

Stage D: trans-2-Benzyl-8-methoxy-1,3,3a,4,9b-pentahydro-(1)-benzopyrano[3,4-c]pyrrole hydrochloride The expected product is obtained according to the process described in Stage D of Example 1, starting with the compound obtained in the above stage.

Elemental microanalysis:

|  | C % | H % | N % | Cl % |
| --- | --- | --- | --- | --- |
| calculated | 68.77 | 6.68 | 4.22 | 10.68 |
| found | 68.34 | 6.67 | 4.22 | 10.56 |

EXAMPLE 10 trans-8-Methoxy-1,3,3a,4,9b-pentahydro-(1)-benzopyrano[3,4-c]pyrrole hydrochloride The expected product is obtained according to the process described in Example 4, starting with the compound obtained in Example 9.

Elemental microanalysis:

|  | C % | H % | N % | Cl % |
| --- | --- | --- | --- | --- |
| calculated | 59.63 | 6.67 | 5.79 | 14.62 |
| found | 59.58 | 6.60 | 5.77 | 14.30 |

EXAMPLE 11 trans-2-Propyl-8-methoxy-1,3,3a,4,9b-pentahydro-(1)-benzopyrano[3,4-c]pyrrole hydrochloride The expected product is obtained according to the process described in Example 6, starting with the compound described in Example 10. Chromatographic purification is performed using a dichloromethane/methanol mixture (95/5) as eluent, and gives the hydrochloride.

Elemental microanalysis:

|  | C % | H % | N % | Cl % |
| --- | --- | --- | --- | --- |
| calculated | 63.48 | 7.88 | 4.94 | 12.49 |
| found | 63.05 | 7.66 | 4.97 | 12.51 |

EXAMPLE 12 cis-2-Benzyl-1,3,3a,4,9b-pentahydro-(1)-benzopyrano[3,4-c]pyrrole hydrochloride

Stage A: cis-1-Benzyl-3-hydroxyphenyl-4-(2-hydroxyphenyl)pyrrolidine 125 mmol of cis-2-benzyl-1,3,3a,9b-tetrahydrobenzopyrano[3,4-c]pyrrol-4-one (described in Preparation D) are added to a heterogeneous solution containing 310 mmol of lithium aluminum hydride in 800 ml of THF at 5° C. The reaction medium is kept stirring for 3 hours at room temperature and is then cooled to +10 C. 120 ml of ethyl alcohol, 120 ml of water and then 40 ml of aqueous 40 % sodium hydroxide solution are successively added. After filtration of the salts, the filtrate is washed with saturated sodium bicarbonate solution. The organic phase is dried and, after evaporation, gives the expected product.

Stage B: cis-1-Benzyl-3-chloromethyl-4-(2-hydroxyphenyl)pyrrolidine hydrochloride The expected product is obtained according to the process described in Stage C of Example 1, starting with the compound described in the above stage.

Stage C: cis-2-Benzyl-1,3,3a,4,9b-pentahydro-(1)-benzopyrano[3,4-c]pyrrole hydrochloride The expected product is obtained according to the process described in Stage D of Example 1, starting with the compound obtained in the above stage.

Elemental microanalysis:

|  | C % | H % | N % | Cl % |
| --- | --- | --- | --- | --- |
| calculated | 71.63 | 6.68 | 4.64 | 11.75 |
| found | 71.46 | 6.29 | 4.98 | 11.62 |

EXAMPLE 13 cis-1,3,3a,4,9b-Pentahydro-(1)-benzopyrano[3,4-c]pyrrole hydrochloride

The expected product is obtained according to the process described in Example 4, starting with the compound obtained in Example 12.

Elemental microanalysis:

|  | C % | H % | N % | Cl % |
| --- | --- | --- | --- | --- |
| calculated | 62.41 | 6.67 | 6.62 | 16.75 |
| found | 61.77 | 6.47 | 6.43 | 16.54 |

EXAMPLE 14 cis-2-Benzyl-9-hydroxy-1,3,3a,4,9b-pentahydro-(1)-benzopyrano[3,4-c]pyrrole hydrochloride Stage A: cis-1-Benzyl-3-hydroxymethyl-4-(2,6-dimethoxyphenyl)pyrrolidine The expected product is obtained according to the process described in Stage A of Example 12, starting with methyl [cis-1-benzyl-4-(2,6-dimethoxyphenyl)pyrrolidin-3-yl] carboxylate described in Preparation E.

Stage B: cis-1-Benzyl-3-chloromethyl-4-(2,6-dimethoxyphenyl)pyrrolidine

The expected product is obtained according to the process described in Stage C of Example 1, starting with the compound described in the above stage.

Stage C: cis-1-Benzyl-3-chloromethyl-4-(2,6-dihydrophenyl)pyrrolidine hydrochloride To 8.9 mmol of the compound obtained in the above stage, in 170 ml of dichloromethane, are added 44.5 ml of a 1M solution of boron tribromide in dichloromethane. The reaction medium is maintained at reflux for 8 hours and then treated with concentrated sodium hydroxide for one hour. The medium is then neutralized using hydrochloric acid. After extraction with dichloromethane, the expected product is obtained after purification of the residue by column chromatography on silica, using a dichloromethane/methanol mixture (95/5) as eluent.

Stage D: cis-2-Benzyl-9-hydroxy-1,3,3a,4,9b-pentahydro-(1)-benzopyrano[3,4-c]pyrrole hydrochloride The expected product is obtained according to the process described in Stage D of Example 1.

Elemental microanalysis:

|  | C % | H % | N % | Cl % |
| --- | --- | --- | --- | --- |
| calculated | 68.03 | 6.34 | 4.41 | 4.26 |
| found | 67.43 | 6.50 | 4.38 | 10.66 |

EXAMPLE 15 cis-2-Benzyl-9-methoxy-1,3,3a,4,9b-pentahydro-(1)-benzopyrano[3,4-c]pyrrole hydrochloride 11.6 mmol of the compound obtained in Example 14, in 50 ml of DMF, are added to a solution containing 14 mmol of sodium hydride in 50 ml of DMF. After stirring for 30 minutes, 11.6 mmol of methyl iodide are added. After 1 hour at room temperature, followed by hydrolysis, the solvents are evaporated off. The residue is then taken up in water. After extraction with ether, drying and evaporation, the expected product is obtained after purification of the residue by column chromatography on silica, using a cyclohexane/ethyl acetate mixture (75/25) as eluent.

Elemental microanalysis:

|  | C % | H % | N % | Cl % |
|---|---|---|---|---|
| calculated | 68.77 | 6.68 | 4.22 | 10.68 |
| found | 68.66 | 4.48 | 4.45 | 10.97 |

EXAMPLE 16 cis-9-Methoxy-1,3,3a,4,9b-pentahydro-(1)-benzopyrano[3,4-c]pyrrole hydrochloride The expected product is obtained according to the process described in Example 4, starting with the compound described in Example 15.

Elemental microanalysis:

|  | C % | H % | N % | Cl % |
|---|---|---|---|---|
| calculated | 59.63 | 6.67 | 5.79 | 14.67 |
| found | 59.97 | 6.69 | 5.93 | 13.87 |

EXAMPLE 17 cis-2-Acetyl-9-methoxy-1,3,3a,4,9b-pentahydro-(1)-benzopyrano[3,4-c]pyrrole

The expected product is obtained according to the process described in Example 5, starting with the compound described in Example 16.

Elemental microanalysis

|  | C % | H % | N % |
|---|---|---|---|
| calculated | 68.00 | 6.93 | 5.68 |
| found | 67.89 | 6.94 | 5.49 |

EXAMPLE 18 trans-2-Benzyl-7-chloro-1,3,3a,4,9b-pentahydro-(1)-benzopyrano[3,4-c]pyrrole hydrochloride Stage A: trans-1-Benzyl-3-hydroxymethyl-4-(2-methoxy-4-chlorophenyl)pyrrolidine The expected product is obtained according to the process described in Stage A of Example 1, using methyl [trans-1-benzyl-4-(2-methoxy-4-chlorophenyl)pyrrolidin-3-yl] carboxylate, described in Preparation F, as starting material.

Stage B: trans-1-Benzyl-3-hydroxymethyl-4-(2-hydroxy-4-chlorophenyl)pyrrolidine

The expected product is obtained according to the process described in Stage B of Example 9, starting with the compound obtained in the above stage.

Stage C: trans-1-Benzyl-3-chloromethyl-4-(2-hydroxy-4-chlorophenyl)pyrrolidine

The expected product is obtained according to the process described in Stage C of Example 1, starting with the compound obtained in the above stage.

Stage D: trans-2-Benzyl-7-chloro-1,3,3a,4,9b-pentahydro-(1)-benzopyrano3,4-c]pyrrole hydrochloride The expected product is obtained according to the process described in Stage D of Example 3 (using two equivalents of sodium hydride), starting with the compound obtained in the above stage.

Elemental microanalysis:

|  | C % | H % | N % | Cl % |
|---|---|---|---|---|
| calculated | 64.29 | 5.70 | 4.17 | 21.09 |
| found | 64.25 | 5.72 | 4.03 | 21.27 |

EXAMPLE 19 cis-2-[2-(Thiochroman-8-yloxy)ethyl]-1,3,3a,9b-pentahydro-(1)-benzopyrano[3,4-c]pyrrole hydrochloride To 4.7 mmol of cis-1,3,3a,4,9b-pentahydro-(1)-benzopyrano[3,4-c]pyrrole hydrochloride, described in Example 13, in 50 ml of acetonitrile are added 9.4 mmol of potassium carbonate. After stirring for 15 min, 0.5mmol of potassium iodide and then 4.7mmol of 1-chloro-2-(thiochroman-8-yloxy)ethane dissolved in 50 ml of acetonitrile are successively added. The reaction medium is maintained at reflux for 24 hours and then evaporated, taken up in water, extracted with dichloromethane and dried over magnesium sulfate before being filtered. The solvents are evaporated off. The crude product is purified by column chromatography on silica (eluent: $CH_2Cl_2/MeOH$: 97/3). The product is then salified by a solution of HCl in ethanol.

Elemental microanalysis:

|  | C % | H % | N % | Cl % | S % |
|---|---|---|---|---|---|
| calculated | 65.41 | 6.49 | 3.47 | 8.78 | 7.94 |
| found | 65.08 | 6.31 | 3.58 | 8.23 | 8.23 |

EXAMPLE 20 cis-2-[(Pyrid-3-yl)aminocarbonyl]-1,3,3a,4,9b-pentahydro-(1)-benzopyrano[3,4-c]pyrrole hydrochloride To 30 mmol of the product obtained in Example 16 in 50 ml of dichloromethane is added 0.15 mmol of 3-pyridyl isocyanate. After stirring for 48 hours, the product is filtered off and then chromatographed on a column of silica (eluent: dichloromethane/methanol: 95/5). The product obtained is salified using ethanolic hydrochloric acid solution.

Elemental microanalysis:

|  | C % | H % | N % | Cl % |
|---|---|---|---|---|
| calculated | 59.75 | 5.57 | 11.61 | 9.80 |
| found | 60.06 | 5.56 | 11.38 | 8.94 |

EXAMPLE 21 cis-2-Benzyl-7-methoxy-1,3,3a,4,9b-pentahydro-(1)-benzopyrano[3,4-c]pyrrole hydrochloride Stage A: cis-1-Benzyl-3-hydroxymethyl-4-(2-hydroxy-4-methoxyphenyl)pyrrolidine To 230 mmol of lithium aluminum hydride in 800 ml of THF, under a nitrogen atmosphere, are added 180 mmol of cis-2-benzyl-7-methoxy-1,3,3a,9b-tetrahydrobenzopyrano [3,4-c]pyrrol-4-one, described in Preparation G, at +5° C. The reaction medium is maintained at +10° C. for one hour before being hydrolyzed, and is filtered on Celite. The organic phase is dried and, after evaporation, gives the expected product.

Stage B: cis-2-Benzyl-7-methoxy-1,3,3a,4,9b-pentahydro-(1)-benzopyrano[3,4-c]pyrrole hydrochloride To 93 mmol of the compound obtained in Stage A in 700 ml of tetrahydrofuran (THF) are successively added 93 mmol of diethyl azodicarboxylate and 93 mmol of triphenylphosphine. The reaction medium is stirred for 3 hours at room temperature and the solvents are then evaporated off. The crude product is purified by column chromatography on silica (eluent: cyclohexane/ethyl acetate: 70/30). The product is salified using a solution of hydrochloric acid in ethanol.

Elemental microanalysis:

|            | C %   | H %  | N %  | Cl %  |
|------------|-------|------|------|-------|
| calculated | 68.77 | 6.68 | 4.22 | 10.68 |
| found      | 69.01 | 6.74 | 4.16 | 10.70 |

EXAMPLE 22 trans-2-Benzyl-7-methoxy-1,3,3a,4,9b-pentahydro-(1)-benzopyrano[3,4-c]pyrrole hydrochloride Stage A: trans-1-Benzyl-3-hydroxymethyl-4-(2,4-dimethoxyphenyl)pyrrolidine The expected product is obtained according to the process described in Stage A of the Example 1, using the compound described in Preparation H.

Stage B: trans-1-Benzyl-3-hydroxymethyl-4-(2-hydroxy-4-methoxyphenyl)pyrrolidine The expected product is obtained according to the process described in Stage B of Example 1, using the compound obtained in the above stage as starting material.

Stage C: trans-2-Benzyl-7-methoxy-1,3,3a,4,9pentahydro-(1)-benzopyrano[3,4-c]pyrrole hydrochloride The expected product is obtained according to the process described in Stage B of Example 21, starting with the compound obtained in the above stage.

Elemental microanalysis:

|            | C %   | H %  | N %  | Cl %  |
|------------|-------|------|------|-------|
| calculated | 68.77 | 6.68 | 4.22 | 10.68 |
| found      | 68.44 | 6.59 | 4.49 | 10.77 |

EXAMPLE 23 trans-2-Benzyl-6-methoxy-1,3,3a,4,9b-pentahydro-(1)-benzopyrano[3,4-c]pyrrole hydrochloride The expected product is obtained according to Stages A, B and C of Example 23, starting with the compound obtained from Preparation I.

Elemental microanalysis:

|            | C %   | H %  | N %  | Cl %  |
|------------|-------|------|------|-------|
| calculated | 68.77 | 6.68 | 4.22 | 10.68 |
| found      | 67.93 | 6.66 | 4.10 | 10.55 |

EXAMPLE 24 cis-2-Benzyl-8-chloro-1,3,3a,4,9b-pentahydro-(1)-benzopyrano[3,4-c]pyrrole hydrochloride Stage A: cis-1-Benzyl-3-hydroxymethyl-4-(2-hydroxy-5-chlorophenyl)pyrrolidine The expected product is obtained according to the process described in Stage A of Example 12, using the compound described in Preparation J as starting material.

Stage B: cis-2-Benzyl-8-chloro-1,3,3a,4,9b-pentahydro-(1)-benzopyrano[3,4-c]pyrrole hydrochloride The expected product is obtained according to the process described in Stage B of Example 21, starting with the compound obtained in the above stage.

Elemental microanalysis:

|            | C %   | H %  | N %  | Cl %  |
|------------|-------|------|------|-------|
| calculated | 64.29 | 5.70 | 4.17 | 21.09 |
| found      | 64.82 | 5.82 | 4.19 | 20.82 |

EXAMPLE 25 trans-2-Benzyl-8-chloro-1,3,3a,4,9b-pentahydro-(1)-benzopyrano[3,4-c]pyrrole hydrochloride The expected product is obtained according to Stages A, B and C of Example 22, starting with the compound obtained from Preparation K.

Elemental microanalysis:

|            | C %   | H %  | N %  | Cl %  |
|------------|-------|------|------|-------|
| calculated | 64.29 | 5.70 | 4.17 | 21.09 |
| found      | 64.01 | 6.01 | 4.22 | 21.05 |

EXAMPLE 26 cis-2-Benzyl-6-chloro-1,3,3a,4,9b-pentahydro-(1)-benzopyrano[3,4-c]pyrrole hydrochloride The expected product is prepared according to Stage A of Example 12 and then Stage B of Example 21, starting with the compound obtained in Preparation L.

Elemental microanalysis:

|            | C %   | H %  | N %  | Cl %  |
|------------|-------|------|------|-------|
| calculated | 64.29 | 5.70 | 4.17 | 21.09 |
| found      | 63.72 | 5.59 | 4.26 | 24.16 |

EXAMPLE 27 trans-2-Benzyl-6-chloro-1,3,3a,4,9b-pentahydro-(1)-benzopyrano[3,4-c]pyrrole hydrochloride The expected product is obtained according to Stages A, B and C of Example 1 and then according to Stage D of Example 3, starting with the compound obtained in Preparation M.

Elemental microanalysis:

|  | C % | H % | N % | Cl % |
|---|---|---|---|---|
| calculated | 64.29 | 5.70 | 4.17 | 21.09 |
| found | 64.22 | 5.45 | 4.01 | 21.47 |

EXAMPLE 28 trans-2-Benzyl-8-bromo-1,3,3a,4,9b-pentahydro-(1)-benzopyrano[3,4-c]pyrrole hydrochloride The expected product is obtained according to Stages A, B and C of Example 1 followed by Stage D of Example 3, starting with the compound obtained in Preparation N.

Elemental microanalysis:

|  | C % | H % | N % | Br % | Cl % |
|---|---|---|---|---|---|
| calculated | 56.79 | 5.03 | 3.68 | 20.99 | 9.31 |
| found | 57.14 | 5.19 | 3.48 | 20.00 | 9.18 |

EXAMPLE 29 trans-2-Benzyl-8-cyano-1,3,3a,4,9b-pentahydro-(1)-benzopyrano[3,4-c]pyrrole hydrochloride 9 mmol of the compound of Example 18 are dissolved in 10.4 ml of dimethylformamide. 5 mmol of zinc cyanide and 0.3 mmol of tetrakis(triphenylphosphine)palladium are then added. The reaction medium is maintained at 80° C. for 6 hours. After cooling, 30 ml of toluene are added and the mixture is washed with twice 20 ml of 2M aqueous ammonia solution and then using saturated sodium chloride solution. After evaporation of the solvents, the crude product is salified using a solution of hydrochloric acid in ethanol.

Elemental microanalysis:

|  | C % | H % | N % | Cl % |
|---|---|---|---|---|
| calculated | 69.83 | 5.86 | 8.57 | 10.85 |
| found | 69.41 | 5.77 | 8.53 | 10.83 |

EXAMPLE 30 trans-8-Cyano-1,3,3a,4,9b-pentahydro-(1)-benzopyrano[3,4-c]pyrrole hydrochloride 17.2 mmol of the compound obtained in Example 29 in 130 ml of ethanol and 40 ml of water are hydrogenated for 24 hours at 40° C. in the presence of 500 mg of palladium-on-charcoal as catalyst. After evaporation of the solvents, the expected product is obtained.

Elemental microanalysis:

|  | C % | H % | N % | Cl % |
|---|---|---|---|---|
| calculated | 60.89 | 5.54 | 11.83 | 14.98 |
| found | 60.44 | 5.52 | 11.45 | 14.26 |

EXAMPLE 31 trans-2-Propyl-8-cyano-1,3,3a,4,9b-pentahydro-(1)-benzopyrano[3,4-c]pyrrole hydrochloride The compound obtained in Example 30 is treated according to the procedure described for Example 6.

Elemental microanalysis:

|  | C % | H % | N % | Cl % |
|---|---|---|---|---|
| calculated | 64.63 | 6.87 | 10.05 | 12.72 |
| found | 63.93 | 6.78 | 9.53 | 12.21 |

EXAMPLE 32 trans-2-Benzyl-1,2,3,3a,4,11c-hexahydro-5-oxa-2-aza-cyclopenta[c]phenanthrene hydrochloride The expected product is obtained according to Stages A, B and C of Example 1 followed by Stage D of Example 3, starting with the compound obtained in Preparation O.

Elemental microanalysis:

|  | C % | H % | N % | Cl % |
|---|---|---|---|---|
| calculated | 75.10 | 6.30 | 3.98 | 10.08 |
| found | 74.51 | 6.25 | 4.16 | 10.02 |

EXAMPLE 33 trans-1,2,3,3a,4,11c-Hexahydro-5-oxa-2-aza-cyclopenta[c]phenanthrene hydrochloride The product obtained in Example 32 is treated according to the procedure of Example 30.

Elemental microanalysis:

|  | C % | H % | N % | Cl % |
|---|---|---|---|---|
| calculated | 68.83 | 6.16 | 5.35 | 13.54 |
| found | 68.49 | 6.25 | 4.99 | 13.47 |

EXAMPLE 34 trans-16-Benzyl-12,13,14,15,16,17-hexahydro-11-oxa-16-aza-cyclopenta[a]phenanthrene hydrochloride The expected product is obtained according to Stage A of Example 1 and then treated according to the procedures described in Stage C of Example 2 and Stage B of Example 21, starting with the compound of Preparation P.

Elemental microanalysis:

|  | C % | H % | N % | Cl % |
|---|---|---|---|---|
| calculated | 75.10 | 6.30 | 3.98 | 10.08 |
| found | 74.89 | 6.30 | 3.93 | 10.19 |

EXAMPLE 35 cis-16-Benzyl-12,13,14,15,16,17-hexahydro-11-oxa-16-aza-cyclopenta[a]phenanthrene hydrochloride The expected product is obtained according to Stages A and B of Example 21, starting with the compound obtained in Preparation Q.

Elemental microanalysis:

|  | C % | H % | N % | Cl % |
|---|---|---|---|---|
| calculated | 75.10 | 6.30 | 3.98 | 10.08 |
| found | 74.53 | 6.38 | 3.85 | 10.02 |

EXAMPLE 36 cis-12,13,14,15,16,17-Hexahydro-11-oxa-16-aza-cyclopenta[a]phenanthrene hydrochloride The expected product is obtained according to the process described for Example 30, starting with the compound of Example 35.

Elemental microanalysis:

|  | C % | H % | N % | Cl % |
|---|---|---|---|---|
| calculated | 68.83 | 6.16 | 5.35 | 13.54 |
| found | 68.41 | 6.22 | 5.56 | 13.46 |

EXAMPLE 37 cis-2-Benzyl-1,2,3,3a,4,11c-hexahydro-5-oxa-2-aza-cyclopenta[c]phenanthrene hydrochloride The expected product is obtained according to Stages A and B of Example 21, starting with the compound obtained in Preparation R.

Elemental microanalysis:

|  | C % | H % | N % | Cl % |
|---|---|---|---|---|
| calculated | 75.10 | 6.30 | 3.98 | 10.08 |
| found | 75.13 | 6.30 | 4.01 | 9.88 |

EXAMPLE 38 cis-1,2,3,3a,4,11c-Hexahydro-5-oxa-2-aza-cyclopenta[c]phenanthrene hydrochloride The expected product is obtained according to the process described for Example 30, starting with the compound of Example 37.

Elemental microanalysis:

|  | C % | H % | N % | Cl % |
|---|---|---|---|---|
| calculated | 68.83 | 6.16 | 5.35 | 13.54 |
| found | 68.25 | 6.11 | 5.43 | 13.19 |

Pharmacological Study of the Compounds of the Invention

EXAMPLE 39

Measurement of the in vitro affinity for the $5\text{-}HT_{2C}$ and $5\text{-}HT_{2A}$ receptors
Methods The procedures described for the studies of the binding to the $5\text{-}HT_{2A}$ and $5\text{-}HT_{2C}$ receptors are exactly those described by H. Canton et al. (Eur. J. Pharmacol., 191, 93, 1990) and M. J. Millan et al. (J. Pharmacol. Exp. Ther., 262, 451–463, 1992). For $5\text{-}HT_{2A}$: rat frontal cortex/[$^3$H]-ketanserin (1.0 nM). For $5\text{-}HT_{2C}$: pig cerebral plexus/[$^3$H]-mesulergine (1.0 nM). The 50% inhibitory doses ($ID_{50}$) are determined by regression analysis and the pKi values are calculated as follows:

$$Ki = \frac{IC_{50}}{1 + [L]/Kd}$$

[L]=concentration of the Kd—Kd=dissociation constant
Results

The results obtained with the reference compounds and the compounds of the invention are combined in the table below.

SB 200,646 showed a modest affinity for the $5\text{-}HT_{2C}$ receptors of the order of 200 nM and had only a weak affinity for the $5\text{-}HT_{2A}$ sites. Its selectivity is thus 6 for the $5\text{-}HT_{2C}$ sites. On the other hand, MDL 100.907 showed a very considerable selectivity of the order of 200 for the $5\text{-}HT_{2A}$ receptors, for which it has a very strong affinity.

The compounds of the invention have a greater affinity for the $5\text{-}HT_{2C}$ receptors than the reference compound SB200, 646. Furthermore, they have a better selectivity for the $5\text{-}HT_{2C}$ receptors with respect to the $5\text{-}HT_{2A}$ receptors.

There may more particularly be mentioned the compounds of Examples 19 and 20, which are 9 and 14 times more powerful antagonists respectively than the reference compound SB 200,646, and the compounds of Examples 6 and 7, which have a selectivity which is twice that of the reference compound SB 200,646.

| Compound | $5\text{-}HT_{2C}$ Ki (nM) | $5\text{-}HT_{2A}$ Ki (nM) | $5\text{-}HT_{2A}/5\text{-}HT_{2C}$ affinity ratio |
|---|---|---|---|
| Example 2 | 195 | 490 | 2.5 |
| Example 3 | 48 | 269 | 5.6 |
| Example 4 | 431 | 3468 | 8.0 |
| Example 6 | 104 | 1738 | 16.7 |
| Example 7 | 120 | 1820 | 15.2 |
| Example 8 | 107 | 95 | 0.9 |
| Example 9 | 468 | 1097 | 2.3 |
| Example 10 | 2188 | >10000 | >4.8 |
| Example 11 | 4074 | >10000 | >2.3 |
| Example 12 | 832 | 3549 | 4.3 |
| Example 13 | 3090 | >10000 | >3.33 |
| Example 14 | 218.8 | 1096 | 5.00 |
| Example 15 | 36.3 | 389.0 | 10.7 |
| Example 16 | 263 | 3311 | 12.6 |
| Example 18 | 871 | 1867 | 2.1 |
| Example 19 | 22 | 155 | 7.0 |
| Example 20 | 14.4 | 102 | 7.1 |
| Example 21 | 871 | 617 | 0.7 |
| Example 22 | 478 | 170 | 3.6 |
| Example 24 | 38 | 107 | 2.8 |
| Example 33 | 51 | 107 | 2.1 |
| Example 34 | 776 | 1479 | 1.9 |
| Example 35 | 331 | 955 | 2.9 |
| Example 36 | 25.7 | 257 | 10 |
| Example 37 | 155 | 1349 | 8.7 |
| Example 38 | 22.9 | 97.7 | 4.3 |
| SB 200,646 | 204.0 | 1318 | 6.5 |
| MDL 100,907 | 107.2 | 0.59 | 0.006 |

Each value represents the average of two to four determinations.

EXAMPLE 40

Pharmaceutical composition Formula for the preparation of 1000 tablets containing a 10 mg dose:

| | |
|---|---|
| Compound of Example 16 | 10 g |
| Hydroxypropylcellulose | 2 g |
| Wheat starch | 10 g |
| Lactose | 100 g |
| Magnesium stearate | 3 g |
| Talc | 3 g |

We claim:
1. A compound selected from these of formula (I):

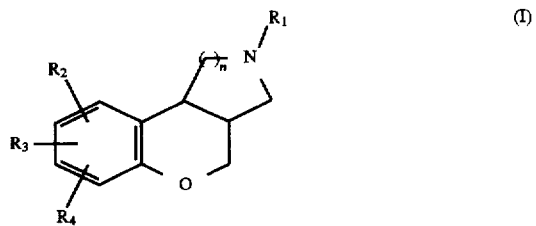

(I)

in which:
n represents 1,
$R_1$ represents hydrogen or linear or branched ($C_1$–$C_6$) alkyl, benzyl, acetyl, benzoyl, allyl, pyridinecarbonyl, pyridinemethyl, pyridineaminocarbonyl, linear or branched ($C_1$–$C_6$) phthalimidoalkyl, linear or branched ($C_1$–$C_4$) (thiochroman-8-yloxy)alkyl, linear or branched ($C_1$–$C_4$) (benzodioxanyloxy)alkyl, or linear or branched ($C_1$–$C_6$) acylaminoalkyl, wherein acyl is benzoyl, naphthylcarbonyl, thienylcarbonyl, linear or branched ($C_1$–$C_6$) alkylcarbonyl, furylcarbonyl, pyrrolylcarbonyl, pyridinylcarbonyl, or ($C_3$–$C_7$) cycloalkylcarbonyl, each of these acyl groups being optionally substituted with one or more halogen, trihalomethyl, alkoxy or hydroxy,
$R_4$ represent hydrogen,
and $R_2$ and $R_3$ are located on adjacent carbons, and form, with the carbon atoms which bear them, a furan or phenyl ring,
the optical isomers thereof and the addition salts thereof with a pharmaceutically-acceptable acid.

2. A compound of formula (I) as claimed in claim 1, in which $R_1$ represents a benzyl group, the optical isomers thereof and the addition salts thereof with a pharmaceutically-acceptable acid.

3. A method for treating a living animal body afflicted with a requiring condition requiring an antagonist to the 5-$HT_{2C}$ receptors comprising the step of administering to the living body an amount of a compound of claim 1 which is effective for alleviation of said condition.

4. A pharmaceutical composition comprising as active principle an effective 5-$HT_{2C}$ receptor-antagonistic amount of a compound as claimed in claim 1, together with one or more pharmaceutically-acceptable excipients or vehicles.

5. A compound of claim 1 selected from the group consisting of:

trans-2-benzyl-1,2,3,3a,4,11c-hexahydro-5-oxa-2-aza-cyclopenta[c]phenanthrene hydrochloride;
trans-1,2,3,3a,4,11c-hexahydro-5-oxa-2-aza-cyclopenta[c]phenanthrene hydrochloride;
trans-16-benzyl-12,13,14,15,16,17-hexahydro-11-oxa-16-aza-cyclopenta[a]phenanthrene hydrochloride;
cis-16-benzyl-12,13,14,15,16,17-hexahydro-11-oxa-16-aza-cyclopenta[a]phenanthrene hydrochloride;
cis-12,13,14,15,16,17-hexahydro-11-oxa-16-aza-cyclopenta[a]phenanthrene hydrochloride;
cis-2-benzyl-1,2,3,3a,4,11c-hexahydro-5-oxa-2-aza-cyclopenta[c]phenanthrene hydrochloride; and
cis-1,2,3,3a,4,11c-hexahydro-5-oxa-2-aza-cyclopenta[c]phenanthrene hydrochloride.

6. A method of claim 3 wherein the compound is selected from the group consisting of:

trans-2-benzyl-1,2,3,3a,4,11c-hexahydro-5-oxa-2-aza-cyclopenta[c]phenanthrene hydrochloride;
trans-1,2,3,3a,4,11c-hexahydro-5-oxa-2-aza-cyclopenta[c]phenanthrene hydrochloride;
trans-16-benzyl-12,13,14,15,16,17-hexahydro-11-oxa-16-aza-cyclopenta[a]phenanthrene hydrochloride;
cis-16-benzyl-12,13,14,15,16,17-hexahydro-11-oxa-16-aza-cyclopenta[a]phenanthrene hydrochloride;
cis-12,13,14,15,16,17-hexahydro-11-oxa-16-aza-cyclopenta[a]phenanthrene hydrochloride;
cis-2-benzyl-1,2,3,3a,4,11c-hexahydro-5-oxa-2-aza-cyclopenta[c]phenanthrene hydrochloride; and
cis-1,2,3,3a,4,11c-hexahydro-5-oxa-2-aza-cyclopenta[c]phenanthrene hydrochloride.

7. A composition of claim 4 wherein the compound is selected from the group consisting of:

trans-2-benzyl-1,2,3,3a,4,11c-hexahydro-5-oxa-2-aza-cyclopenta[c]phenanthrene hydrochloride;
trans-1,2,3,3a,4,11c-hexahydro-5-oxa-2-aza-cyclopenta[c]phenanthrene hydrochloride;
trans-16-benzyl-12,13,14,15,16,17-hexahydro-11-oxa-16-aza-cyclopenta[a]phenanthrene hydrochloride;
cis-16-benzyl-12,13,14,15,16,17-hexahydro-11-oxa-16-aza-cyclopenta[a]phenanthrene hydrochloride;
cis-12,13,14,15,16,17-hexahydro-11-oxa-16-aza-cyclopenta[a]phenanthrene hydrochloride;
cis-2-benzyl-1,2,3,3a,4,11c-hexahydro-5-oxa-2-aza-cyclopenta[c]phenanthrene hydrochloride; and
cis-1,2,3,3a,4,11c-hexahydro-5-oxa-2-aza-cyclopenta[c]phenanthrene hydrochloride.

* * * * *

UNITED STATES PATENT AND TRADEMARK OFFICE
CERTIFICATE OF CORRECTION

PATENT NO. : 5,723,484
DATED : March 3, 1998
INVENTOR(S) : G. Lavielle, T. Dubuffet, M. Millan, A. Newman-Tancredi Page 1 of 2

It is certified that error appears in the above-indentified patent and that said Letters Patent is hereby corrected as shown below:

Column 1, line 7: Insert:
-- TITLE OF THE INVENTION

The present invention relates to new benzopyran compounds. --.

Column 2, line 29: Insert -- which -- between "antagonist" and "may".

Column 9, line 29: "R4" should read -- $R_4$ --.

Column 10, line 26: Delete the word "the".

Column 21, lines 33, 34 & 35: Beginning with the words -- Stage A.... -- these lines should begin a new paragraph.

Column 21, line 46: "1,3,3a,4,9pentahydro-" should read -- 1,3,3a,4,9b-pentahydro- --.

Column 22, line 28 (approx.): "2082" should read --20.81--.

UNITED STATES PATENT AND TRADEMARK OFFICE
CERTIFICATE OF CORRECTION

PATENT NO. : 5,723,484
DATED : March 3, 1998
INVENTOR(S) : G. Lavielle, T. Dubuffet, M. Millan, A. Newman-Tancredi It is certified that error appears in the above-indentified patent and that said Letters Patent is hereby corrected as shown below:

Column 26, lines 66 & 67: Beginning with "Formula....", this line should begin a new paragraph.

Column 27. line 41: Delete "formula (I) as claimed in".

Column 27, line 46: Delete the word "requiring" before "condition".

Signed and Sealed this

Sixteenth Day of June, 1998

Attest:

BRUCE LEHMAN

Attesting Officer

Commissioner of Patents and Trademarks